(12) United States Patent
Wechter

(10) Patent No.: US 9,364,658 B2
(45) Date of Patent: Jun. 14, 2016

(54) ELECTRICAL STIMULATION LEADS WITH MULTIPLE ANCHORING UNITS AND METHODS OF MAKING AND USING

(71) Applicant: BOSTON SCIENTIFIC NEUROMODULATION CORPORATION, Valencia, CA (US)

(72) Inventor: David Ernest Wechter, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/634,253

(22) Filed: Feb. 27, 2015

(65) Prior Publication Data

US 2015/0246217 A1    Sep. 3, 2015

Related U.S. Application Data

(60) Provisional application No. 61/947,126, filed on Mar. 3, 2014.

(51) Int. Cl.
*A61N 1/00* (2006.01)
*A61N 1/05* (2006.01)

(52) U.S. Cl.
CPC ............... *A61N 1/05* (2013.01); *A61N 1/0558* (2013.01)

(58) Field of Classification Search
CPC ............................. A61N 1/0558; A61N 1/057
USPC ........................................................ 607/119
See application file for complete search history.

(56) References Cited

U.S. PATENT DOCUMENTS

| | | |
|---|---|---|
| 4,706,682 A | 11/1987 | Stypulkowski et al. |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |

(Continued)

FOREIGN PATENT DOCUMENTS

| | | |
|---|---|---|
| WO | 2004028618 | 4/2004 |
| WO | 2005028023 | 3/2005 |

(Continued)

OTHER PUBLICATIONS

International Search Report and Written Opinion for PCT Application No. PCT/US2015/018100 mailed Aug. 26, 2015.

(Continued)

*Primary Examiner* — Nicole F Lavert
(74) *Attorney, Agent, or Firm* — Lowe Graham Jones PLLC; Bruce E. Black

(57) ABSTRACT

An electrical stimulation lead includes a lead body; electrodes disposed along a distal end portion of the lead body; terminals disposed along a proximal end portion of the lead body; conductors electrically coupling the terminals to the electrodes; and anchoring units disposed along the distal end portion of the lead body. First and second anchoring units each have a wide end portion and a narrow end portion. The first anchoring unit is disposed closer to the proximal end portion of the lead body than any of the other anchoring units. The wide end portion of the first anchoring unit is disposed closer to the proximal end portion of the lead body than the narrow end portion. The narrow end portion of the second anchoring unit is disposed closer to the proximal end portion of the lead body than the wide end portion.

20 Claims, 8 Drawing Sheets

(56) References Cited

U.S. PATENT DOCUMENTS

| | | |
|---|---|---|
| 6,741,892 B1 | 5/2004 | Meadows et al. |
| 6,999,819 B2 | 2/2006 | Swoyer et al. |
| 7,244,150 B1 | 7/2007 | Brase et al. |
| 7,328,068 B2 | 2/2008 | Spinelli et al. |
| 7,343,202 B2 | 3/2008 | Mrva et al. |
| 7,369,894 B2 | 5/2008 | Gerber |
| 7,437,193 B2 | 10/2008 | Parramon et al. |
| 7,565,198 B2 | 7/2009 | Bennett et al. |
| 7,672,734 B2 | 3/2010 | Anderson et al. |
| 7,761,165 B1 | 7/2010 | He et al. |
| 7,881,783 B2 | 2/2011 | Bonde et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2003/0195600 A1* | 10/2003 | Tronnes ............ A61N 1/05  607/116 |
| 2005/0288722 A1 | 12/2005 | Eigler et al. |
| 2007/0150036 A1 | 6/2007 | Anderson |
| 2008/0103572 A1 | 5/2008 | Gerber |
| 2008/0167701 A1 | 7/2008 | John et al. |
| 2008/0183253 A1 | 7/2008 | Bly |
| 2009/0012592 A1 | 1/2009 | Buysman et al. |
| 2009/0054949 A1 | 2/2009 | Alexander et al. |
| 2009/0248095 A1* | 10/2009 | Schleicher ........... A61N 1/0558  607/2 |
| 2009/0254151 A1 | 10/2009 | Anderson et al. |
| 2010/0131036 A1 | 5/2010 | Geistert et al. |
| 2010/0168806 A1 | 7/2010 | Norlin-Weissenrieder et al. |
| 2010/0256696 A1 | 10/2010 | Schleicher et al. |
| 2012/0053665 A1 | 3/2012 | Stolz et al. |
| 2013/0066411 A1 | 3/2013 | Thacker et al. |
| 2014/0343645 A1 | 11/2014 | Wechter |
| 2014/0343656 A1 | 11/2014 | Wechter |

FOREIGN PATENT DOCUMENTS

| | | |
|---|---|---|
| WO | 2013082283 | 6/2013 |
| WO | 2015167800 | 11/2015 |

OTHER PUBLICATIONS

U.S. Appl. No. 14/690,071, filed Apr. 17, 2015.
U.S. Appl. No. 14/634,253, filed Feb. 27, 2015.
U.S. Appl. No. 62/111,596, filed Feb. 3, 2015.
U.S. Appl. No. 62/006,824, filed Jun. 2, 2014.

* cited by examiner

ELECTRICAL STIMULATION LEADS WITH MULTIPLE ANCHORING UNITS AND METHODS OF MAKING AND USING

CROSS-REFERENCE TO RELATED APPLICATIONS

This application claims the benefit under 35 U.S.C. §119 (e) of U.S. Provisional Patent Application Ser. No. 61/947,126, filed Mar. 3, 2014, which is incorporated herein by reference.

FIELD

The present invention is directed to the area of implantable electrical stimulation systems and methods of making and using the systems, and in particular implantable electrical stimulation leads having anchoring units interspersed with electrodes and methods of making and using the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

One concern regarding implanted leads is lead migration. This may occur over time and result in movement of the lead away from the desired tissue for stimulation so as to reduce the effectiveness of therapeutic treatment.

BRIEF SUMMARY

One embodiment is an electrical stimulation lead including a lead body having a distal end portion, a proximal end portion, and a longitudinal length; electrodes disposed along the distal end portion of the lead body; terminals disposed along the proximal end portion of the lead body; conductors electrically coupling the terminals to the electrodes; and anchoring units disposed along the distal end portion of the lead body. The anchoring units include a first anchoring unit and a second anchoring unit, and the first and second anchoring units each have a wide end portion and a narrow end portion. A largest outer radius of the wide end portion is larger than a largest outer radius of the narrow end portion. The first anchoring unit is disposed closer to the proximal end portion of the lead body than any of the other anchoring units. The wide end portion of the first anchoring unit is disposed closer to the proximal end portion of the lead body than the narrow end portion of the first anchoring unit. The narrow end portion of the second anchoring unit is disposed closer to the proximal end portion of the lead body than the wide end portion of the second anchoring unit.

Another embodiment is an electrical stimulation lead including a lead body having a distal end portion, a proximal end portion, and a longitudinal length; electrodes disposed along the distal end portion of the lead body; terminals disposed along the proximal end portion of the lead body; conductors electrically coupling the terminals to the electrodes; and anchoring units disposed along the distal end portion of the lead body. At least one of the anchoring units forms a wide end arrangement that includes a distal end portion, a proximal end portion, and a middle portion. The proximal end portion and distal end portion of the wide end arrangement each have a largest outer radius that is larger than a largest outer radius of the middle portion of the wide end arrangement.

Alternatively or additionally, at least one of the anchoring units forms a wide center arrangement with a distal end portion, a proximal end portion, and a middle portion. The proximal end portion and distal end portion of the wide center arrangement each have a largest outer radius that is smaller than a largest outer radius of the middle portion of the wide center arrangement.

Alternatively or additionally, at least one of the anchoring units forms a combination arrangement that includes a distal end portion, a proximal end portion, a wide middle portion, and a narrow middle portion. The proximal end portion and the wide middle portion of the combination arrangement each have a largest outer radius that is larger than a largest outer radius of each of the distal end portion and the narrow middle portion of the combination arrangement. The narrow middle portion is positioned between the proximal end portion and the wide middle portion and the wide middle portion is positioned between the distal end portion and the narrow middle portion.

Yet another embodiment is an electrical stimulation lead including a lead body having a distal end portion, a proximal end portion, and a longitudinal length; electrodes disposed along the distal end portion of the lead body; terminals disposed along the proximal end portion of the lead body; conductors electrically coupling the terminals to the electrodes; and anchoring units disposed along the distal end portion of the lead body. Each of the anchoring units includes a lead attachment element and multiple fins. Each fin is attached to, and extends away from, the lead attachment element. The anchoring units include a first anchoring unit and a second anchoring unit. The first and second anchoring units each have a wide portion where the fins extend furthest from the lead attachment element and a narrow portion where the fins extend least from the lead attachment element. The first anchoring unit is disposed closer to the proximal end portion of the lead body than any of the other anchoring units. The wide portion of the first anchoring unit is disposed closer to the proximal end portion of the lead body than the narrow portion of the first anchoring unit. The narrow portion of the second anchoring unit is disposed closer to the proximal end portion of the lead body than the wide portion of the second anchoring unit.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems, and in particular implantable electrical stimulation leads having anchoring units interspersed with electrodes and methods of making and using the leads.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Applications Publication Nos. 2007/0150036 and 2010/0256696, all of which are incorporated by reference.

Figure 1:
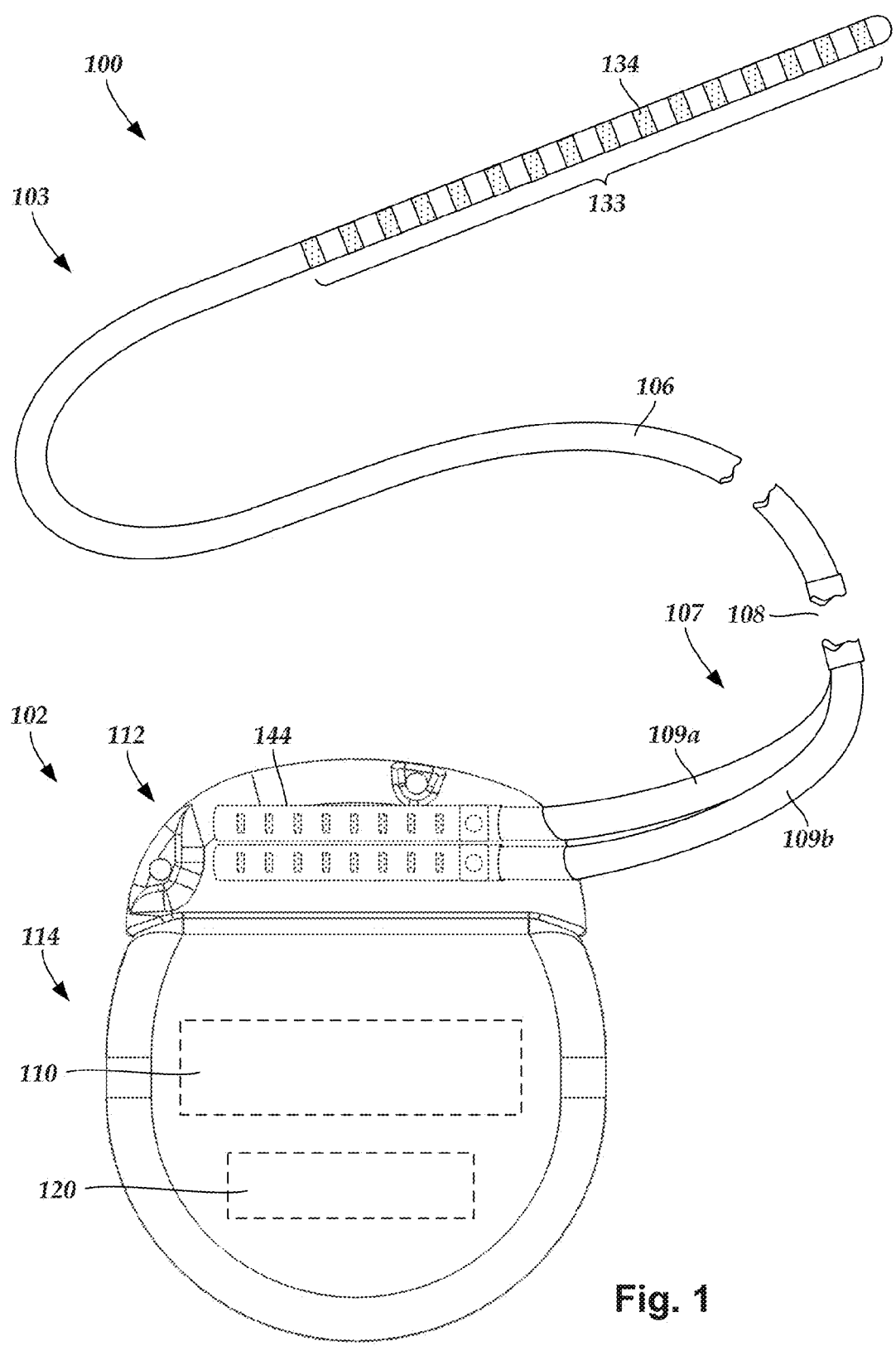
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
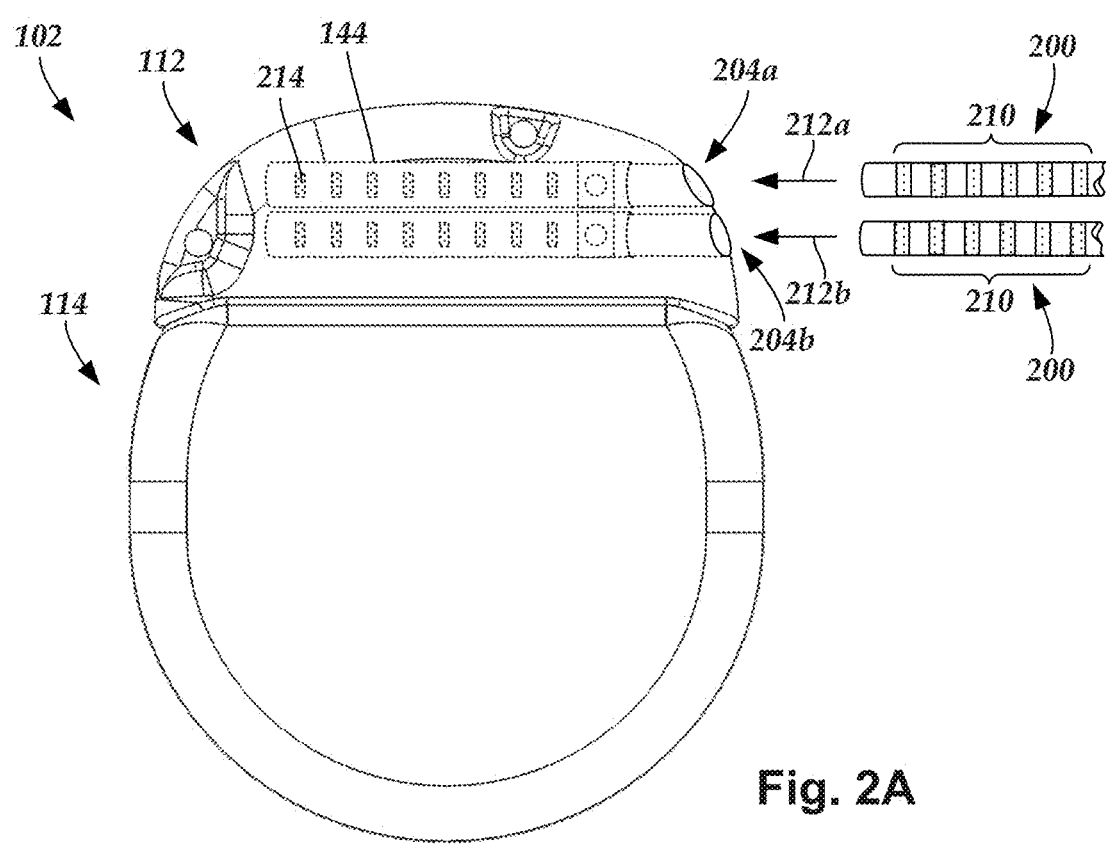
FIG. 2A is a schematic side view of one embodiment of the control module of FIG. 1 configured and arranged to electrically couple to an elongated device, according to the invention.
Figure 2B:
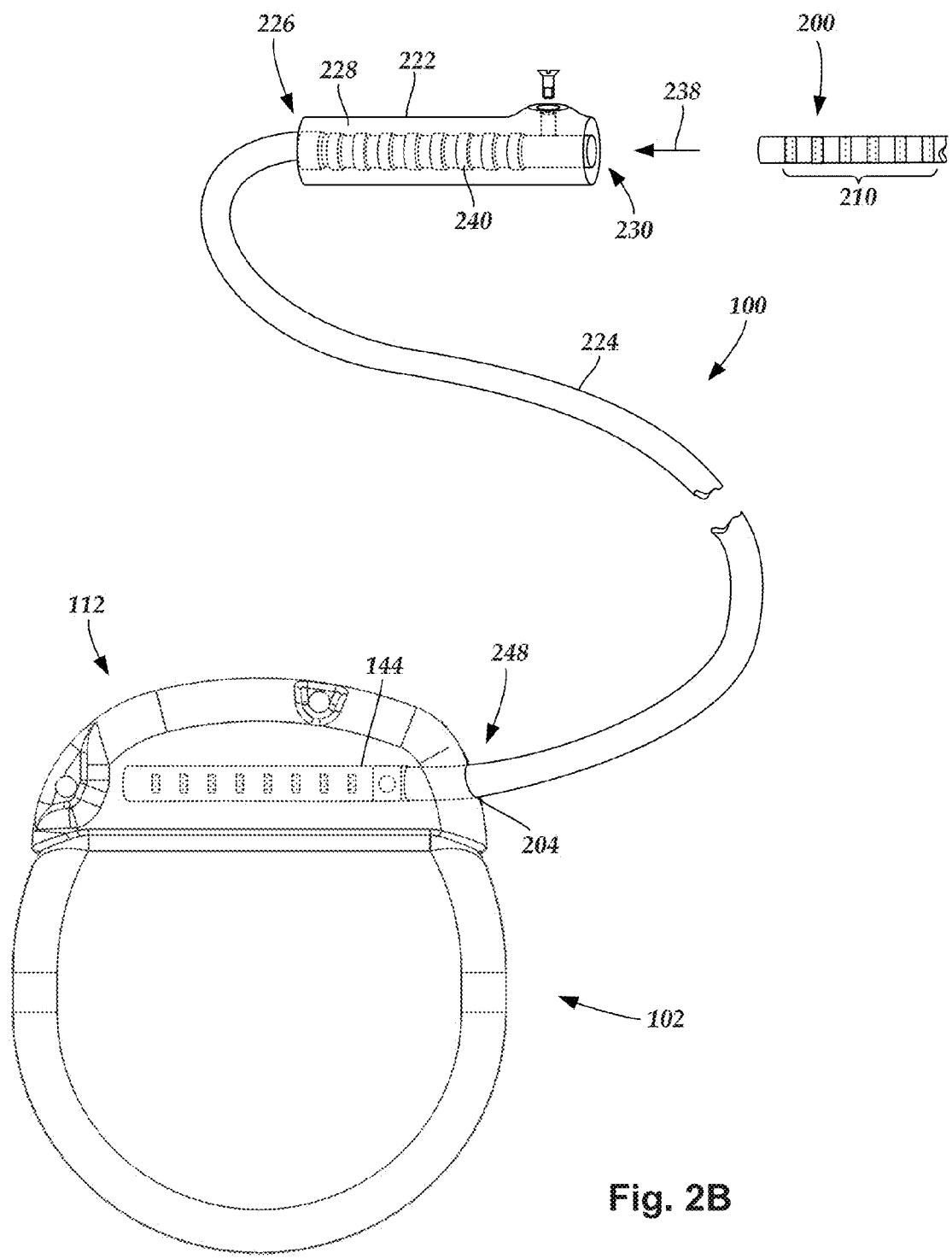
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Lead anchoring units can be attached to the lead to facilitate anchoring the lead into patient tissue. The term "tissue" includes, but is not limited to, muscular tissue, connective tissue, organ tissue, bone, cartilage, nerve tissue, and the like. These lead anchoring units, as opposed to conventional lead anchors, can be delivered with the lead through an introducer during the implantation process. The lead anchoring units include anchoring elements that lodge against patient tissue and prevent or reduce lateral or axial (or both lateral and axial) migration of the lead after implantation. The lead anchoring units can be particularly useful for leads for sacral nerve stimulation, spinal cord stimulation, or the stimulation of other patient tissue and organs.

Figure 3:
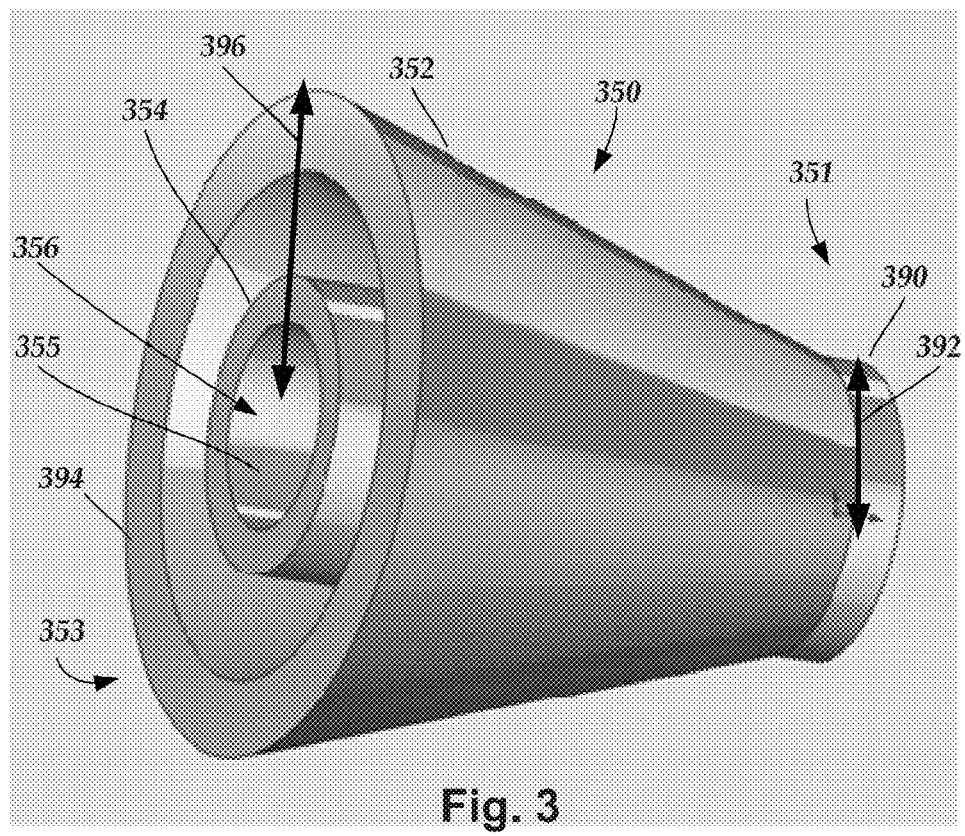
FIG. 3 is a schematic perspective view of one embodiment of a lead anchoring unit, according to the invention.
Figure 6:
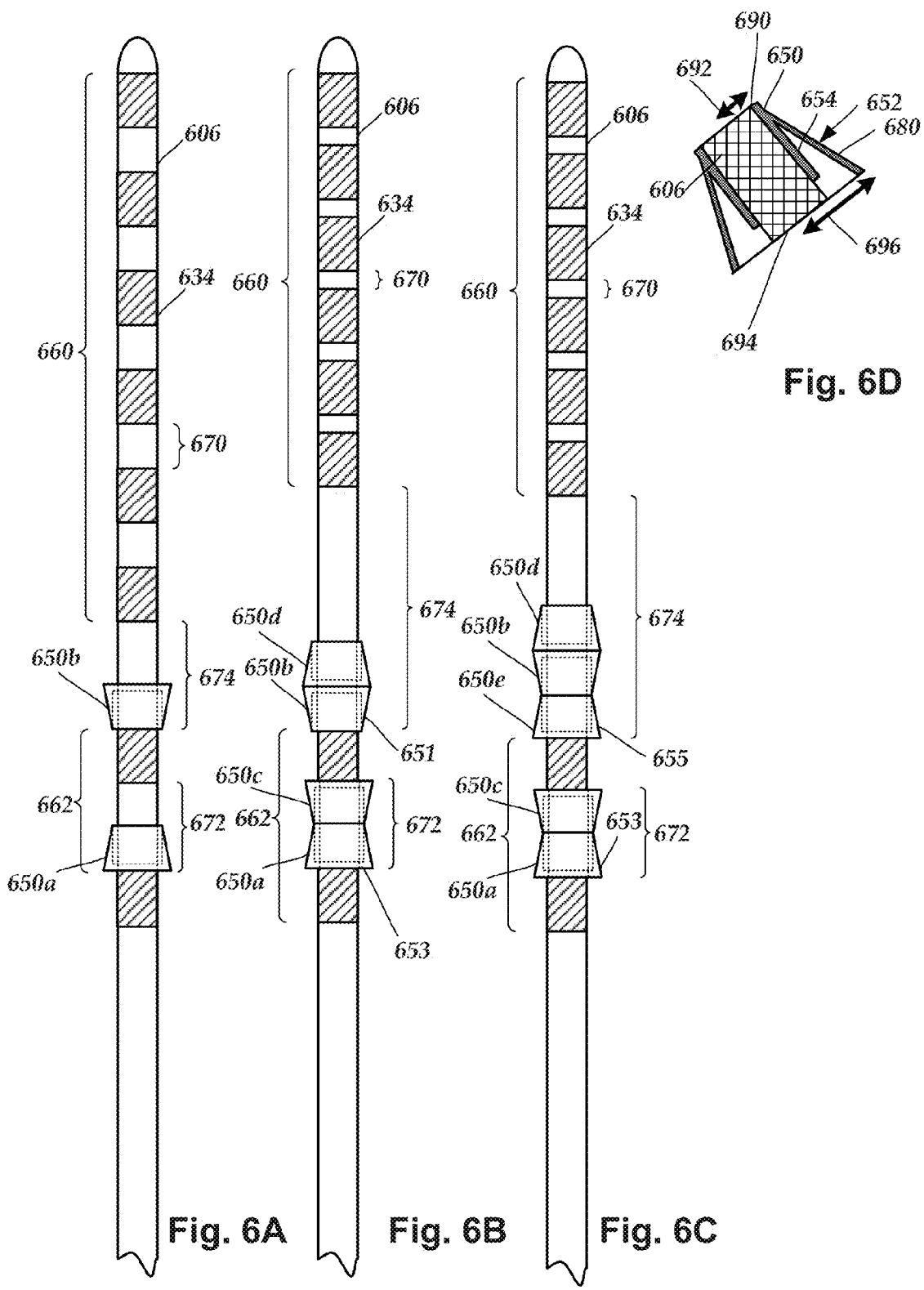
FIG. 6A is a schematic side view of one embodiment of a distal portion of a lead with lead anchoring units disposed thereon, according to the invention.
FIG. 6B is a schematic side view of another embodiment of a distal portion of a lead with lead anchoring units disposed thereon, according to the invention.
FIG. 6C is a schematic side view of a third embodiment of a distal portion of a lead with lead anchoring units disposed thereon, according to the invention.
FIG. 6D is a schematic cross-sectional view of a portion of the lead body and one of the lead anchoring units of FIG. 6A, according to the invention.

FIG. 3 is a schematic perspective view of one embodiment of a lead anchoring unit 350 that will be disposed along a distal end portion of a lead body (e.g., the lead body 106 as shown in FIG. 1 or the lead body 606 of FIG. 6A). The lead anchoring unit 350 facilitates anchoring the lead body to the surrounding tissue when implanted within a patient's body.

The anchoring unit 350 includes a lead attachment element 354 having a tube-shaped (e.g., cylindrical) configuration. As shown, the lead attachment element 354 has a first end 351, a second end 353, and a central lumen 356 extending between the two ends 351, 353. The central lumen 356 may be referred to as an "attachment lumen 356". The attachment lumen 356 is employed to receive at least a portion of the lead body of a lead. In at least some embodiments, the lead attachment element 354 has a circular cross-section. However, the lead attachment element 354 can be formed of any other suitable shape, including shapes having an elliptical, rectangular, polygonal, irregular, or any other suitable lateral cross-section. The lead attachment element 354 can have a uniform lateral cross-section along its entire length or a varying lateral cross-section along its length. In at least some embodiments, the cross-section and dimensions of the lead attachment element 354 are dictated by the configuration of the lead body. In at least some embodiments, the outer diameter of the lead body may be slightly larger than the diameter of the attachment lumen 356 so that the lead attachment element fits snuggly on the lead body.

In at least some embodiments, an interior surface 355 of the lead attachment element 354 may be patterned to assist in maintaining the position of the lead anchoring unit on the lead. The pattern may be regular or irregular and may include features, such as, but not limited to, surface roughening, cutouts, grooves, regular or irregular shapes, or the like. In at least some embodiments, an outer surface of the lead body 106 may be patterned. The pattern may be regular or irregular and may include features, such as, but not limited to, surface roughening, cutouts, grooves, regular or irregular shapes, or the like. In some embodiments, both the interior surface 355 of the lead attachment element 354 and the outer surface of the lead body are patterned. The patterning of the lead attachment element 354 and the lead body may be complementary. In at least some embodiments, the pattern on the interior surface 355 of the lead attachment element 354 and the pattern on the exterior surface of the lead body can be generated so that the two patterns interlock with each other.

The patterning described above may be formed using any suitable method, including, but not limited to, ablation (e.g., RF or laser ablation), grinding, knurling, chemical etching, or the like. The patterning may be made on the spacers (i.e., between adjacent or consecutive electrodes) of the lead body 106.

The anchoring unit 350 includes at least one anchoring element 352 coupled to the lead attachment element 354. Although the coupling may occur anywhere along the lead attachment element 354, in the illustrated embodiment, the anchoring element 352 is coupled to the lead attachment element 354 at, or immediately adjacent to, its first end 351.

In the illustrated embodiment, the anchoring element 352 includes a cone that extends over the lead attachment element 354. In at least some embodiments, the cone is longer than the lead attachment element 354 so that the cone extends over, and beyond, the lead attachment element 354. In other embodiments, the cone may be shorter than the lead attachment element 354, and only extend over a portion the lead attachment element 354. The anchoring element 352 may have any other suitable shape to interact with patient tissue to anchor the lead to the tissue. Anchoring the lead to the patient's tissue may impede, reduce, mitigate, or prevent lead migration.

Figure 4:
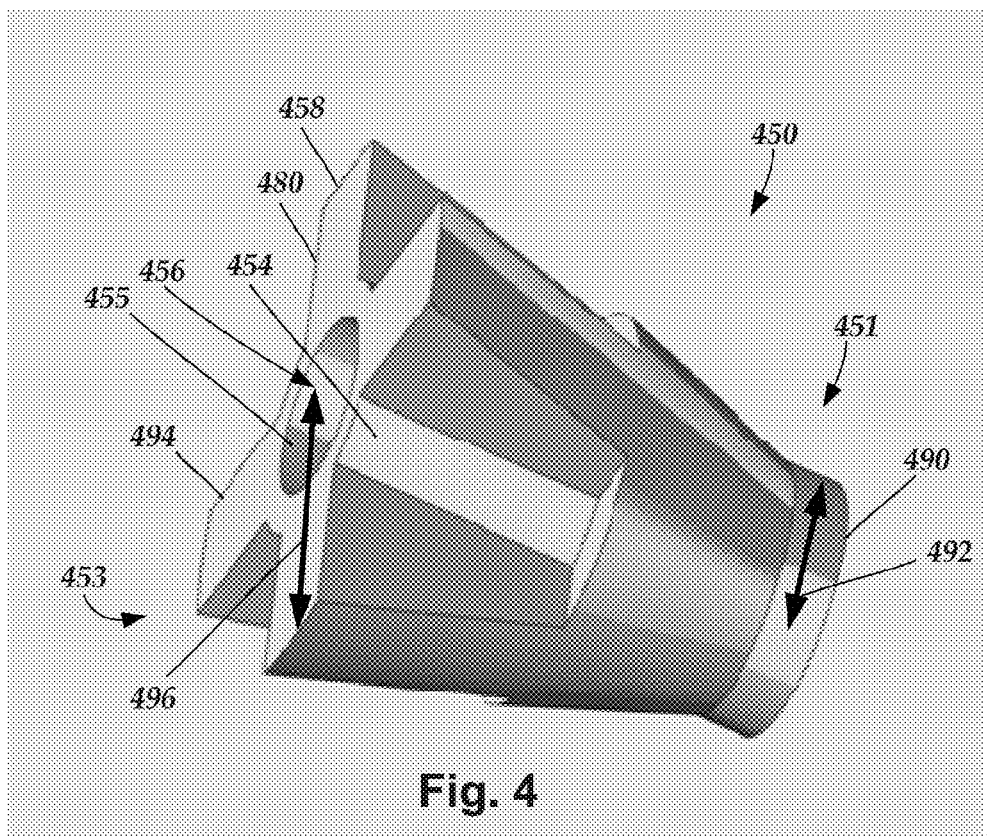
FIG. 4 is a schematic perspective view of a second embodiment of a lead anchoring unit, according to the invention.

In the illustrated embodiment, the anchoring element 352 is disposed over the lead attachment element 354 such that the anchoring unit 350 that is formed has a narrow end portion 390 and a wide end portion 394. The outer radius of the wide end portion 394 varies (as shown in FIG. 4), and defines a largest outer radius 396. In the illustrated embodiment, the outer radius of the narrow end portion 390 is uniform and defines a largest outer radius 392. The largest outer radius 396 of the wide end portion 394 is larger than the outer radius 392 of the narrow end portion 390, such that anchoring unit 350 defines a conical shape. The wide end portion 394 is particularly useful to anchor the attached lead against tissue. The wide end portion 394 can face distally or proximally to resist movement, particularly in the facing direction. The transition from the narrow end portion 390 to the wide end portion 394 may facilitate implantation of the anchoring unit and the attached lead into the tissue or insertion of the anchoring unit and attached lead into an introducer (e.g., a needle or cannula) for implantation.

In at least some embodiments, the anchoring unit 350 is a unitary structure with the anchoring element 352 and the lead attachment element 354 formed together. In other embodiments, the anchoring element 352 may be formed separately and then disposed over (and preferably attached to) the lead attachment element 354 to form the anchoring unit 350.

The anchoring unit 350 may form a friction fit with the lead body to hold the anchoring unit in place. Additionally and alternatively, an adhesive, such as a silicone adhesive, may be employed to bond the anchoring unit 350 to the lead body.

The anchoring unit 350 may be formed of any suitable material, such as any suitable biocompatible material including, but not limited to, metals, polymers, alloys, or the like. In at least some embodiments, the anchoring unit 350 is formed of silicone, polyurethane, or the like. In some embodiments, the material that is used has a stiffness that is sufficient to anchor the lead body to the surrounding tissue, while also having sufficient flexibility to reduce, or in some cases avoid, damage or injury to the tissue or to facilitate delivery of the lead with the anchoring unit(s) through an introducer.

In particular, the anchoring unit 350 may be configured to facilitate deployment through an introducer, such as a needle or cannula. In at least some embodiments, the anchoring unit 350 is sufficiently pliable so that it can be compressed within an introducer during implantation. When the introducer is removed, the anchoring unit 350 may then expand to anchor the lead body 106 to the tissue.

FIG. 4 illustrates a second embodiment of a lead anchoring unit 450 that includes a lead attachment element 454 and at least one anchoring element 458. The lead attachment element 454 receives and attaches to a portion of a lead body 106. The at least one anchoring element 458 anchor the lead body to the patient's tissue.

The lead attachment element 454 has a tube-shaped (e.g., cylindrical) configuration, and includes a first end 451, a second end 453, and a central lumen 456 extending therebetween. The central lumen 456 may also be referred to as "attachment lumen 456". In at least some embodiments, the lead attachment element 454 has a circular lateral cross-section. However, the lead attachment element 454 can be formed of any other suitable shape, including shapes having an elliptical, rectangular, polygonal, irregular, or any other suitable cross-section. The lead attachment element 454 can have a uniform lateral cross-section along its entire length or a varying lateral cross-section along its length. In at least some embodiments, the cross-section and dimensions of the lead attachment element 454 are dictated by the configuration of the lead body. In at least some embodiments, the outer diameter of the lead body may be slightly larger than the diameter of the attachment lumen 456.

In at least some embodiments, an interior surface 455 of the lead attachment element 454 may be patterned to assist in maintaining the position of the lead anchoring unit 450 on the lead. The pattern may be regular or irregular and may include features, such as, but not limited to, surface roughening, cutouts, grooves, regular or irregular shapes, or the like. In at least some embodiments, an outer surface of the lead body 106 may be patterned. The pattern may be regular or irregular and may include features, such as, but not limited to, surface roughening, cutouts, grooves, regular or irregular shapes, or the like. In some embodiments, both the interior surface 455 of the lead attachment element 454 and the outer surface of the lead body are patterned. The patterning of the lead attachment element 454 and the lead body may be complementary.

In at least some embodiments, the pattern on the interior surface 455 of the lead attachment element 454 and the pattern on the exterior surface of the lead body can be generated so that the two patterns interlock with each other.

The patterning described above may be formed using any suitable method, including, but not limited to, ablation (e.g., RF or laser ablation), grinding, knurling, chemical etching, or the like. The patterning may be made on the spacers (i.e., between adjacent or consecutive electrodes) of the lead body 106.

The anchoring unit 450 may form a friction fit with the lead body to hold the anchoring unit in place. Additionally and alternatively, an adhesive, such as a silicone adhesive, may be employed to bond the anchoring unit 450 to the lead body.

The anchoring element(s) 458 are disposed around the lead attachment element 454 and extend away radially from the lead attachment element 454. In the illustrated embodiment, the anchoring elements 458 are fins 480. Any number of fins 480 (or other attachment elements) can be used. The embodiment shown in FIG. 4 includes four fins 480 disposed about the circumference of the lead attachment element 454. The fins 480 shown in FIG. 4 have a trapezoid-shaped configuration, but it will be recognized that the fins 480 can have any suitable shape including, but not limited to, triangular, rectangular, irregular, and the like. Any suitable number of fins 480 may be disposed about the circumference of the lead attachment element 454 including, but not limited to, two, three, four, five, six, seven, eight, or more fins. The fins 480 can be spaced apart uniformly or non-uniformly around the circumference of the lead attachment element 454. In some embodiments, the fins 480 form an angle of ninety degrees with the lead attachment element 454 as illustrated in FIG. 4, but the fins 480 could extend at a different angle from the lead attachment element 454 (for example, an angle in the range from 30 to 85 degrees).

The fins 480 are shown in FIG. 4 as extending along a partial length of the lead attachment element 454, while being disposed about the circumference of the lead attachment element 454. However, in some other embodiments, such as the embodiment shown in FIG. 5, the fins 480 can extend along an entire length of the lead attachment element 454. In some embodiments, the anchoring unit 450 is a unitary structure with the anchoring element(s) 458 and the lead attachment element 454 formed together. In other embodiments, the anchoring element(s) 458 are attached to the lead attachment element 454.

The anchoring unit 450 includes a narrow end portion 490 and a wide end portion 494. As shown, the outer radius of the wide end portion 494 varies and defines a largest outer radius 496. In the illustrated embodiment, the outer radius of the narrow end portion is uniform and defines a largest outer radius 492. The largest outer radius 496 of the wide end portion 494 is larger than the largest outer radius 492 of the narrow end portion 490. The wide end portion 494 is particularly useful to anchor the attached lead against tissue. The wide end portion 494 can face distally or proximally to resist movement, particularly in the facing direction. The transition from the narrow end portion 490 to the wide end portion 494 may facilitate implantation of the anchoring unit and the attached lead into the tissue or insertion of the anchoring unit and attached lead into an introducer (e.g., a needle or cannula) for implantation.

Figure 5:
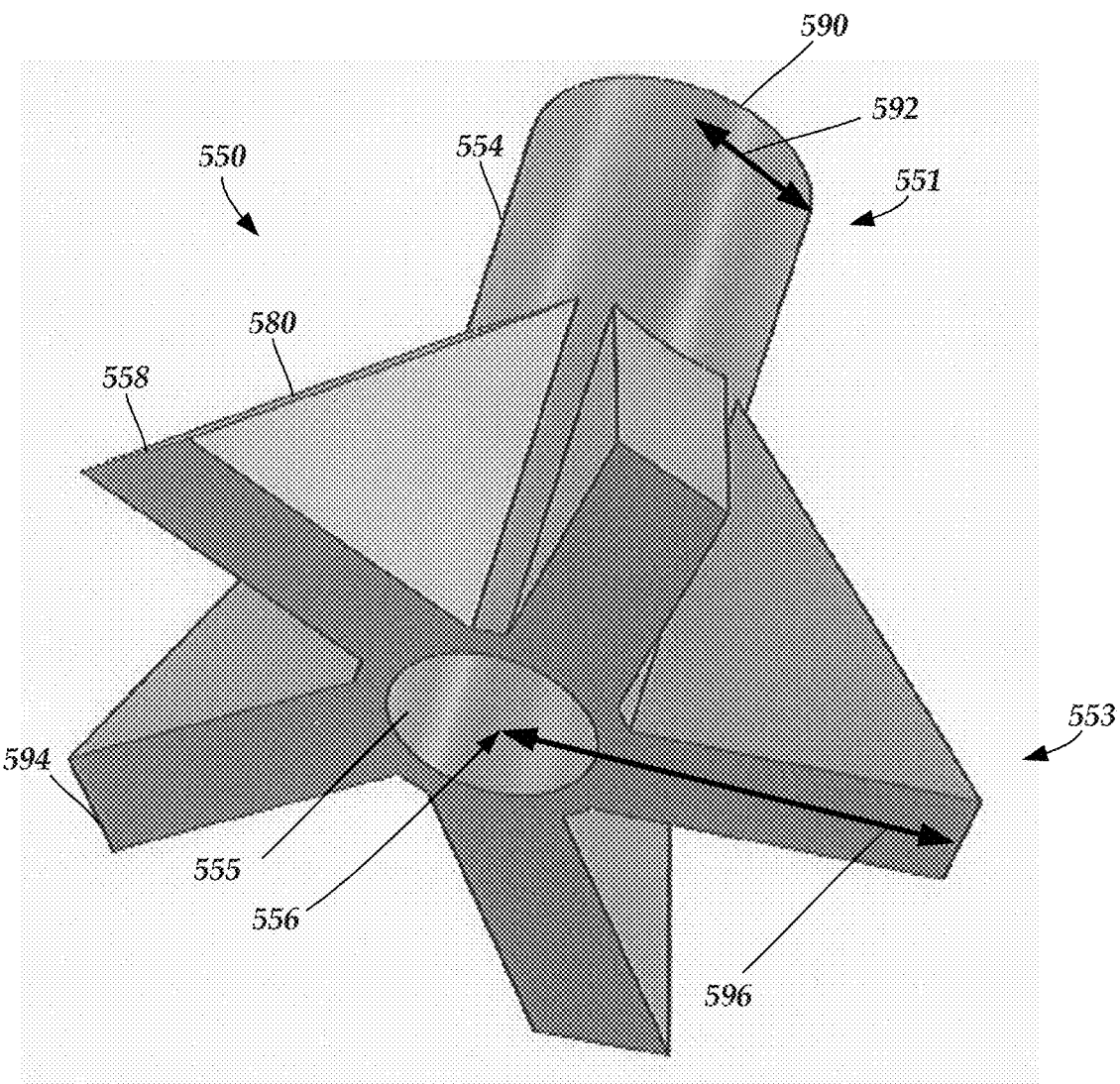
FIG. 5 is a schematic perspective view of a third embodiment of a lead anchoring unit, according to the invention.

FIG. 5 illustrates a third embodiment of a lead anchoring unit 550 that includes a lead attachment element 554 and at least one anchoring element 558. The lead attachment element 554 receives and attaches to a portion of a lead body 106. The at least one anchoring element 558 anchors the lead body to the patient's tissue.

The lead attachment element 554 has a tube-shaped (e.g., cylindrical) configuration, and includes a first end 551, a second end 553, and a central lumen 556 extending therebetween. The central lumen 556 may also be referred to as "attachment lumen 556". In at least some embodiments, the lead attachment element 554 has a circular lateral cross-section. However, the lead attachment element 554 can be formed of any other suitable shape, including shapes having an elliptical, rectangular, polygonal, irregular, or any other suitable cross-section. The lead attachment element 554 can have a uniform lateral cross-section along its entire length or a varying lateral cross-section along its length. In at least some embodiments, the cross-section and dimensions of the lead attachment element 554 are dictated by the configuration of the lead body. In at least some embodiments, the outer diameter of the lead body may be slightly larger than the diameter of the attachment lumen 556.

In at least some embodiments, an interior surface 555 of the lead attachment element 554 may be patterned to assist in maintaining the position of the lead anchoring unit on the lead. The pattern may be regular or irregular and may include features, such as, but not limited to, surface roughening, cutouts, grooves, regular or irregular shapes, or the like. In at least some embodiments, an outer surface of the lead body 106 may be patterned. The pattern may be regular or irregular and may include features, such as, but not limited to, surface roughening, cutouts, grooves, regular or irregular shapes, or the like. In some embodiments, both the interior surface 555 of the lead attachment element 554 and the outer surface of the lead body are patterned. The patterning of the lead attachment element 554 and the lead body may be complementary. In at least some embodiments, the pattern on the interior surface 555 of the lead attachment element 554 and the pattern on the exterior surface of the lead body can be generated so that the two patterns interlock with each other.

The patterning described above may be formed using any suitable method, including, but not limited to, ablation (e.g., RF or laser ablation), grinding, knurling, chemical etching, or the like. The patterning may be made on the spacers (i.e., between adjacent or consecutive electrodes) of the lead body 106.

The anchoring unit 550 may form a friction fit with the lead body to hold the anchoring unit in place. Additionally and alternatively, an adhesive, such as a silicone adhesive, may be employed to bond the anchoring unit 350 to the lead body.

The anchoring element(s) 558 are disposed around the lead attachment element 554 and extend away from the lead attachment element 554. In the illustrated embodiment, the anchoring elements 558 are fins 580. Any number of fins 580 (or other attachment elements) can be used. The embodiment shown in FIG. 5 includes five fins 580 disposed about the circumference of the lead attachment element 554. The fins 580 shown in FIG. 5 have a triangular-shaped configuration, but it will be recognized that the fins 580 can have any suitable shape including, but not limited to, trapezoidal, rectangular, irregular, and the like. Any suitable number of fins 580 may be disposed about the circumference of the lead attachment element 554 including, but not limited to, two, three, four, five, six, seven, eight, or more fins. The fins 580 can be spaced apart uniformly or non-uniformly around the circumference of the lead attachment element 554. In some embodiments, the fins 580 form an angle of ninety degrees with the lead attachment element 554 as illustrated in FIG. 5, but it will be recognized that the fins 580 could extend at a different angle from the lead attachment element 554 (for example, an angle in the range from 30 to 85 degrees).

The fins 580 are shown in FIG. 5 as extending along a partial length of the lead attachment element 554, while being disposed about the circumference of the lead attachment element 554. However, in some other embodiments, such as the embodiment shown in FIG. 5, the fins 580 can extend along an entire length of the lead attachment element 554.

In some embodiments, the anchoring unit 550 includes a narrow end portion 590 and a wide end portion 594. The outer radius of the wide end portion 594 is varying and defines a largest outer radius 596. In the illustrated embodiment, the outer radius of the narrow end portion 590 is uniform and has a largest outer radius 592. The largest outer radius 596 of the wide end portion 594 is larger than the largest outer radius 592 of the narrow end portion 590. The wide end portion 594 is particularly useful to anchor the attached lead against tissue. The wide end portion 594 can face distally or proximally to resist movement, particularly in the facing direction. The transition from the narrow end portion 590 to the wide end portion 594 may facilitate implantation of the anchoring unit and the attached lead into the tissue or insertion of the anchoring unit and attached lead into an introducer (e.g., a needle or cannula) for implantation.

The anchoring units illustrated in FIGS. 3-5 and described above can be useful in anchoring a lead within patient tissue. Examples of other suitable anchoring units can be found in U.S. Patent Application Publication No. 2010/0256696, incorporated herein by reference. When anchoring a lead within tissue, the specific site of placement and configuration of the anchoring units within the tissue can also enhance anchoring. For example, if the lead is to be used to stimulate the sacral nerve and the lead is implanted through the sacral foramen, it may be useful to position at some of the anchoring units on the lead so that they will engage the sacral foramen or tissue (such as the fascia) around the sacral foramen, or any combination thereof. To do so, these anchoring units should be placed at suitable locations along the lead. Stimulation of the sacral nerve can be useful to treat overactive bladder, urinary or fecal incontinence, and the like and other diseases or dysfunctions.

Additionally, different configurations of the anchoring unit may impede, reduce, mitigate, or prevent proximal, as well as distal, migration. Moreover, it has been found that placement of an electrode proximal to the anchoring unit may mechanically stabilize the anchoring unit to prevent or reduce dislodgement or sliding of the anchoring unit from its position on the lead. The electrode may also enhance the anchoring effect of the anchoring unit. Furthermore, placement of electrodes near the anchoring units facilitates identification of the site of the anchoring units by fluoroscopy or similar techniques. The electrodes stand out (are easily viewable or identifiable) on fluoroscopic images, whereas the anchoring units are often made of material similar to the lead body and are often more difficult to identify on fluoroscopic images.

FIGS. 6A, 6B, and 6C illustrate three embodiments of leads with anchoring units, and two different sets of electrodes that are arranged for stimulation and for placement with respect to the anchoring units. It will be understood that these are simply examples of possible electrode arrangements. The anchoring units, and the arrangement of those anchoring units, described herein can be used with any arrangement of electrodes and are not limited to use with the specific electrode arrangements illustrated herein.

In FIGS. 6A, 6B, and 6C, a distal portion of a lead body 606 includes multiple spaced apart electrodes 634. The electrodes 634 are disposed in two distinct sets: a first set 660 and a second set 662. The first set 660 of electrodes is, at least in some embodiments, distal to all of the anchoring units 650 and is primarily positioned to stimulate patient tissue. In contrast, the electrodes of the second set 662 are spaced apart from the first set 660 and are each proximal to one or more of the anchoring units 650.

In at least some embodiments, the electrodes of the second set 662 stabilize or enhance the effect of the anchoring units or assist in identification of the site of the anchoring units on fluoroscopic images. In at least some embodiments, one or more of the electrodes of the second set 662 are positioned to stimulate patient tissue. In at least some embodiments, at least one of the electrodes of the second set 662 is positioned proximal to all of the anchoring units 650, as illustrated in FIGS. 6A, 6B, and 6C.

In the embodiments of FIGS. 6A, 6B, and 6C, six electrodes 634 are disposed on the lead body 606 in the first set 660 in a uniform spaced apart arrangement, however, any suitable number of electrodes 634 can be provided in the first set 660 in any suitable arrangement, including but not limited to two, four, eight, ten, twelve, fourteen, sixteen, or more electrodes or any other number of electrodes. In some embodiments, the distal-most electrode is a tip electrode. In the illustrated embodiment, the electrodes of the first set 660 are spaced apart from each other by a uniform first distance 670. However, it will be understood that the electrode spacing in the first set 660 need not be uniform.

The second set 662 includes two electrodes 634 disposed on the lead body 606 in a spaced apart arrangement. It will be understood that any suitable number of electrodes 634 can be provided in any suitable arrangement, including but not limited to two, three, four, six, eight, ten, twelve, fourteen, sixteen, or more electrodes or any other number of electrodes. In the illustrated embodiments, the electrodes of the second set 662 are spaced apart from each other by a second distance 672. In some alternative embodiments, the second set 662 includes a single electrode, and therefore such embodiments do not have a second distance 672. In other embodiments, the second set includes more than two electrodes and the second distance between the electrodes may or may not be uniform.

In at least some embodiments, the second distance 672 is greater than the first distance 670. Further, the first set 660 is spaced apart from the second set 662 by a third distance 674. In the embodiment of FIG. 6A, the third distance 674 is equal to the second distance 672. However, in the embodiments of FIGS. 6B and 6C, the third distance 674 is greater than the second distance 672. In at least some embodiments, the third distance 674 is at least twice the second distance 672, as illustrated in FIG. 6B. In at least some embodiments, the third distance 674 is at least twice the first distance 672, as illustrated in both FIGS. 6A and 6B, and the third distance 674 can be at least four, five, six, eight, ten, twelve, fourteen, or more times the first distance 672.

The first, second, and third distances 670, 672, and 674, respectively, may be selected or otherwise determined by any suitable method. For example, one or more of the first, second, and third distances 670, 672, and 674 is selected based on the particular anatomy of the patient and the place where the lead is to be implanted. In other embodiments, one or more of the first, second, and third distances 670, 672, and 674 is selected based on the anatomy of the average adult human, average adult male, average adult female, average child, or any other group or subgroup of potential patients, or any other similar criteria. In some embodiments, one or more of the first, second, and third distances 670, 672, and 674 is selected based on an anticipated implantation or stimulation site. In other embodiments, one or more of the first, second, or third distances 670, 672, and 674 is selected to be useful for a range of implantation or stimulation sites. For example, a lead used for spinal cord stimulation includes the electrodes located at a larger distance than that of electrodes on a lead used for deep brain stimulation.

The following are examples of possible size and spacing for the elements of the lead. It will be understood that these are only examples and that leads with elements having other sizes and spacings are suitable for use. In these examples, the electrodes 634 have a longitudinal length in the range of 1 to 5 mm including, for example, in the range of 2 to 4 mm. The first distance 670 is in the range of 0.5 to 4 mm including, for example, 2.5 mm (FIG. 6A) or 1 mm (FIGS. 6B and 6C). The second distance 672 is in the range of 4 to 10 mm including, for example, in the range of 5 to 7 mm. The third distance 674 is in the range of 4 to 20 mm or in the range of 6 to 16 mm including, for example, in the range of 5 to 7 mm (FIG. 6A) or in the range of 12 to 16 mm (FIGS. 6B and 6C).

The leads described herein include at least two anchoring units, one of which is the proximal-most anchoring unit and another is the distal-most anchoring unit. At least some of the anchoring units (and, in some embodiments, all of the anchoring units) include a wide end portion and a narrow end portion. At least one of the anchoring units is placed such that the wide end portion faces proximally (see, e.g., anchoring unit 650a of FIGS. 6A, 6B, and 6C; anchoring unit 650d of FIGS. 6B and 6C; anchoring unit 650e of FIG. 6C; anchoring units 750a, 750d of FIG. 7; and anchoring units 850a, 850d, 850e of FIG. 8) and at least one of the anchoring units is placed such that the wide end portion faces distally (see, e.g., anchoring unit 650b of FIGS. 6A, 6B, and 6C; anchoring unit 650c of FIGS. 6B and 6C; anchoring units 750b, 750c of FIG. 7; and anchoring units 850b, 850c of FIG. 8). In at least some embodiments, the proximal-most anchoring unit is placed such that the wide end portion faces proximally and the distal-most anchoring unit is placed such that the wide end portion faces distally (see, e.g., FIGS. 6A, 6B, 6C, 7, and 8). These configurations resist, impede, or prevent migration of the lead in both the distal and proximal directions.

In FIGS. 6A, 6B, and 6C, one or more of the anchoring units 650 are mounted between the electrodes 634 of the second set 662, and one or more of the electrodes are mounted between the first set 660 and the second set 662. As shown in FIG. 6A, two anchoring units, a first anchoring 650a and a second anchoring unit 650b, are disposed on the lead body 606. The first anchoring unit 650a is disposed closer to a proximal end portion of the lead body 606 than the second anchoring unit 650b. The first anchoring unit 650a is disposed between the electrodes of the second set 662. In some embodiments, the first anchoring unit 650a is disposed such that a wide end portion (e.g., the wide end portion 394 as shown in FIG. 3) of the first anchoring unit 650a is disposed closer to the proximal end portion of the lead body (e.g., the lead body 106 as shown in FIG. 1) than a narrow end portion (e.g., narrow end portion 390 as shown in FIG. 3) of the first anchoring unit 650b. In at least some embodiments, such a placement of the first anchoring unit 650a resists, impedes, or prevents migration of the lead in a proximal direction.

Further, the second anchoring unit 650b is disposed in the space (identified by distance 674) between the first set 660 and the second set 662 of the electrodes, such that all the electrodes of the second set 662 are proximal to the second anchoring unit 650b. Also, at least one of the electrode of the second set 662 is disposed between the first anchoring unit 650a and the second anchoring unit 650b. The second anchoring unit 650b is disposed in a different configuration than that of the first anchoring unit 650a. In the illustrated embodiment, a narrow end portion of the second anchoring unit 650b is disposed closer to the proximal end portion of the lead body than a wide end portion of the second anchoring unit 650b. In some embodiments, such a placement of the second anchoring unit 650b resists, impedes, or prevents migration of the lead in a distal direction. Hence, placing a combination of the first and second anchoring unit 650a, 650b may resist, impede, or prevent migration of the lead in the distal, as well as the proximal, direction.

The embodiment of FIG. 6B includes two more anchoring units, a third anchoring unit 650c and a fourth anchoring unit 650d, in addition to the first and second anchoring units 650a, 650b respectively. In FIG. 6B, the first anchoring unit 650a and the second anchoring unit 650b are similar to the first and the second anchoring unit of FIG. 6A. The third anchoring unit 650c and the fourth anchoring unit 650b each include a wide end portion (e.g., wide end portion 394 as shown in FIG. 3) and a narrow end portion (e.g., narrow end portion 390 as shown in FIG. 3). In some embodiments, the first anchoring unit 650a and the third anchoring unit 650c may be formed integrally or attached to each other prior to sliding on the lead. Similarly, the second anchoring unit 650b and the fourth anchoring unit 650d may be formed integrally or attached to each other prior to sliding onto the lead. In some embodiments, the anchoring units 650a, 650b, 650c, and 650d may be formed separately and thereby constitute separate and discrete elements. The first and third anchoring units 650a, 650c can be spaced apart from each other (for example, separated by at least one mm or more) or these two anchoring units 650a, 650c can be in contact with each other. The second and fourth anchoring units 650b, 650d can be spaced apart from each other (for example, separated by at least one mm or more) or these two anchoring units 650b, 650d can be in contact with each other.

As shown, the third anchoring unit 650c is disposed adjacent the first anchoring unit 650a between the electrodes of the second set 662, such that the narrow end portion of the third anchoring unit 650c is disposed closer to the proximal end portion of the lead body than the wide end portion of the third anchoring unit 650c. In the illustrated embodiment, the first anchoring unit 650a and the third anchoring unit 650c are disposed in a wide end arrangement 653 where the wide end portions of the anchoring units form the ends of the wide end arrangement. In such an arrangement, the wide end portions of the first anchoring unit 650a and the third anchoring unit 650c are disposed away from each other.

The fourth anchoring unit 650d is disposed adjacent, and distal to, the second anchoring unit 650b. The fourth anchoring 650d is disposed such that the wide end portion of the fourth anchoring unit 650d is disposed closer to the proximal end portion of the lead body than the narrow end portion of the fourth anchoring unit 650d. In the illustrated embodiment, the second anchoring unit 650b and the fourth anchoring unit 650d are disposed in a wide center arrangement 653 where the wide end portions of the anchoring units form a center of the wide center arrangement. This arrangement is achieved by disposing the narrow end portions of the anchoring units away from each other. Deployment of the third and fourth anchoring unit 650c, 650d along with first and the second anchoring unit 650a, 650b may eliminate or at least further reduce the chances of lead migration in both proximal and distal directions.

As shown in FIG. 6C, a fifth anchoring unit 650e is disposed in the space (identified by distance 674) adjacent and proximal to the second anchoring unit 650b. In the illustrated embodiment, the fifth anchoring unit 650e is disposed such that a wide end portion (e.g., the wide end portion 394 as shown in FIG. 3) of the fifth anchoring unit 650e is disposed closer to the proximal end of the lead body, while a narrow end portion (e.g., narrow end portion 390 as shown in FIG. 3) of the fifth anchoring unit 650e is in contact with second anchoring unit 650b. The second, fourth, and the fifth anchoring units 650b, 650d, 650e, respectively, form a combination arrangement 655 of three anchoring units. Alternatively, the fifth anchoring unit 650e can be spaced apart from the second anchoring unit 650b (for example, by 1 mm or more). In some embodiments, the second anchoring unit 650b, the fourth anchoring unit 650d, and the fifth anchoring unit 650e (or any combination thereof) may be formed integrally or attached to each other prior to sliding on the lead. In some embodiments, the anchoring units 650b, 650d, and 650e may be formed separately and thereby constitute separate and discrete elements.

Other embodiments can include additional or alternative anchoring units that are mounted elsewhere along the lead. Any suitable number of anchoring units, such as two, three, four, five, six, seven, eight, nine, ten, or more anchoring units, can be used. Factors affecting the number of anchoring unit may include, but are not limited to, length of the lead, location or site of lead implantation, or particular anatomy of the patient. Further, any suitable type of anchoring units described above, including the anchoring units 350, 450, and 550 of FIGS. 3, 4, and 5, respectively, or any of the anchoring units found in U.S. Patent Application Publication No. 2010/0256696, or any other suitable anchoring units may be used. The anchoring units may be all the same type or there may be anchoring units of two or more different types (as examples, a combination of anchoring units 350 and anchoring units 450 or a combination of anchoring units 350 and anchoring units 550 or a combination of anchoring units 550 and anchoring units 450). The anchoring units 650 can contact each other (as illustrated in FIGS. 6A, 6B, and 6C) or can be spaced apart from each other.

FIG. 6D is a cross-sectional view of a portion of the lead body 606 and one anchoring unit 650. The anchoring unit 650 includes an anchoring element 652 and a lead attachment element 654. The lead attachment element 654 has a tubular configuration defining a central attachment lumen (such as attachment lumen 456) that receives a portion of the lead body 606. The anchoring element 652 includes fins 680 that extend radially away from the lead attachment element 654, thereby anchoring the lead to the surrounding tissue.

Further, the fins 680 are disposed such that the anchoring unit 650 includes a narrow end portion 690 and a wide end portion 694. The wide end portion 694 has a largest outer radius 696 that is larger than a largest outer radius 692 of the narrow end portion 690

A variety of methods may be employed to attach the anchoring unit 650 to the lead body 606. For example, each individual anchoring unit 650 can be slid onto the lead body 606 to the desired position along the lead body. In some embodiments, the anchoring unit 650 is swelled prior to sliding on the lead body. As an example, a silicone anchoring unit 650 can be treated with a heptane solution to swell the anchoring unit so that it can be slid onto the lead body. As the heptane evaporates, the anchoring unit 650 returns to its original dimensions. In some embodiments, a portion of the lead body 606 where the anchoring unit 650 is to be placed may be ablated to reduce the diameter of the lead body at that position. In some embodiments, biocompatible adhesive may be used to attach, or enhance attachment, of the anchoring unit 650 to the lead body 606. Such adhesive may be applied prior to, or after, sliding the anchoring unit 650 onto the lead body 606.

Figure 7:
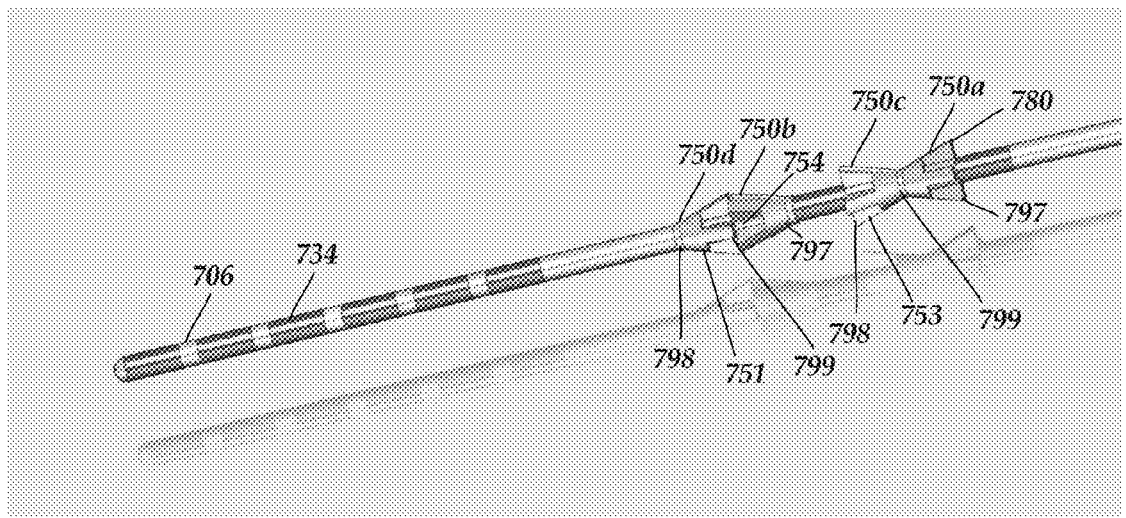
FIG. 7 is a schematic perspective view of a third embodiment of a distal portion of a lead with lead anchoring units disposed thereon, according to the invention.
Figure 8:
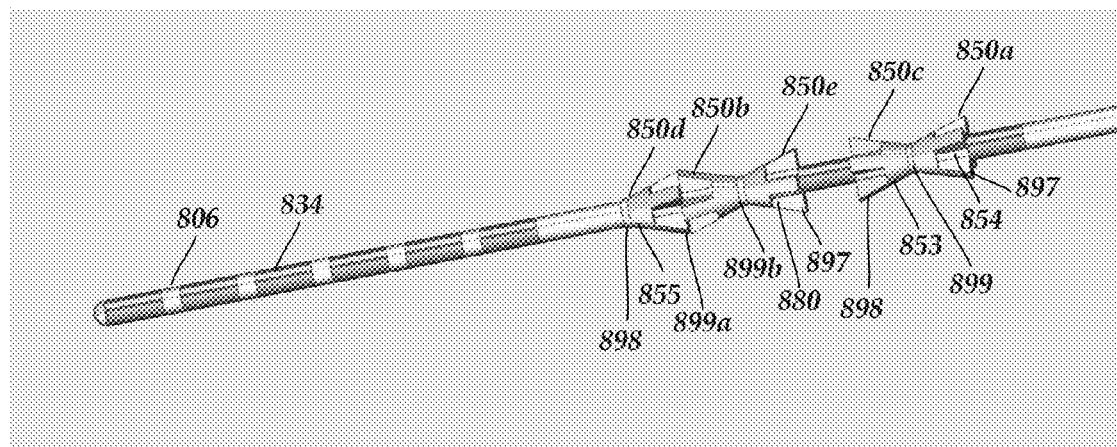
FIG. 8 is a schematic perspective view of a fourth embodiment of a distal portion of a lead with lead anchoring units disposed thereon, according to the invention.

FIGS. 7 and 8 are schematic perspective views of a third embodiment and a fourth embodiment, respectively, of a distal portion of a lead body with lead anchoring units disposed thereon. The distal end portion of the lead body includes multiple electrodes spaced apart in the illustrated arrangements. For instance, in some embodiments, the electrodes are disposed in a uniform spaced apart arrangement. However, in other embodiments, the electrodes are disposed in a non-uniform arrangement.

In these embodiments, one or more anchoring units are disposed on the lead body. The embodiment of FIG. 7 includes four anchoring units, a first anchoring unit 750a, a second anchoring unit 750b, a third anchoring unit 750c, and a fourth anchoring unit 750d. The anchoring units 750a, 750b, 750c, 750d each include a lead attachment element 754 and a number of fins 780 attached to, and extending away from, the lead attachment element 754. In at least some embodiments, the anchoring units 750a, 750b, 750c, 750d include a wide end portion (e.g., the wide end portion 494 as shown in FIG. 4) and the narrow end portion (e.g., the narrow end portion 490 as shown in FIG. 4). In at least some embodiments, the wide end portion is the portion where the fins extend furthest from the lead attachment element 754 and the narrow end portion is the portion where the fins 780 extend least from the lead attachment element 754.

As shown, the second anchoring unit 750b and the fourth anchoring unit 750d are arranged in a wide center arrangement 751 where the wide end portions of both the second and fourth anchoring unit 750b, 750d are arranged adjacent to each other forming a middle portion 799. In some embodiments, the second and fourth anchoring units 750b, 750d are integrally formed as a unitary structure. In other embodiments, the second and fourth anchoring units 750b, 750d are separately formed and disposed together in the wide center arrangement 751. In the illustrated embodiment, the second anchoring unit 750b and the fourth anchoring unit 750d are arranged such that the fins 780 of the anchoring units 750b, 750d are staggered with respect to each other. Such an arrangement of the fins 780 may provide additional stability to resist, impede, or prevent lead migration as the radial ends of the fins are exposed to tissue. In other embodiments, one or more (or even all) of the fins 780 of each of the anchoring units 750b, 750d are aligned with each other.

The wide center arrangement 751 includes a distal end portion 798, a proximal end portion 797, and the middle portion 799. In the wide center arrangement 751, the middle portion 799 corresponds to the wide end portions of the second anchoring unit 750b and fourth anchoring unit 750d, while the proximal end portion 797 corresponds to the narrow end portion of the second anchoring unit 750b, and the distal end portion 798 corresponds to the narrow end portion of the fourth anchoring unit 750d. The outer radius of the middle portion is varying and includes a largest outer radius. The distal and proximal end portions of the illustrated embodiment each have a uniform outer radius that is a largest outer radius at the end portion. The largest outer radius of the middle portion 799 of the wide center arrangement is larger than the largest outer radius of each of the distal and proximal end portions 797, 798.

The first anchoring unit 750a and a third anchoring unit 750c are arranged in a wide end arrangement 753 where the narrow end portions of both the first and the third anchoring unit 750a, 750c are arranged adjacent to each other forming a middle portion 799. In some embodiments, the first and third anchoring units 750a, 750c are integrally formed as a unitary structure. In other embodiments, the first and third anchoring units 750a, 750c are separately formed and disposed together in the wide end arrangement 753. In the illustrated embodiment, the first anchoring unit 750a and the third anchoring unit 750c are arranged such that the fins 780 of the anchoring units 750a, 750c are staggered with respect to each other. In other embodiments, one or more (or even all) of the fins 780 of each of the anchoring units 750a, 750c are aligned with each other.

The wide end arrangement 753 includes a proximal end portion 797, a distal end portion 798, and a middle portion 799. In the wide end arrangement 753, the middle portion 799 is defined by arranging the narrow end portions of the first anchoring unit 750a and the third anchoring unit 750c, while the proximal end portion 797 is defined by the wide end portion of the first anchoring unit 750a and the distal end portion 798 is defined by the wide end portion of the third anchoring unit 750c. The outer radius of each of the distal end portion and the proximal end portion is varying and defines a largest outer radius. In the illustrated embodiment, the middle portion has a uniform outer radius that is a largest outer radius for that portion. The largest outer radius of each of the distal end portion 798 and the proximal end portion 797 is larger than the largest outer radius of the middle portion 799. Any other suitable arrangements of the anchoring units is also possible.

The embodiment of FIG. 8 includes a first anchoring unit 850a, a second anchoring unit 850b, a third anchoring unit 850c, a fourth anchoring unit 850d, and a fifth anchoring unit 850e. The structure and arrangement of the anchoring units 850a, 850b, 850c, 850d, 850e is similar to the structure and arrangement of the anchoring units 750a, 750b, 750c, 750d except as described below. The anchoring units 850a, 850b, 850c, 850d each include a lead attachment element 854 and a number of fins 880 attached to, and extending away from, the lead attachment element 854. The anchoring units 850a, 850b, 850c, 850d, 850e also include a wide end portion and a narrow end portion. The wide end portion can be defined where the fins 880 extend furthest from a lead attachment element 854 and, in the illustrated embodiment, the narrow end portion can be defined where the fins 880 extend least from the lead attachment element 854.

As shown, the first anchoring unit 850a and the third anchoring unit 850c are arranged in a wide end arrangement 853 similar to the wide end arrangement 753 of the embodiment of FIG. 7. The wide end arrangement 853 includes a distal end portion 898, a proximal end portion 897, and a middle portion 899 similar to the distal end portion 798, the proximal end portion 797, and the middle portion 799 of the embodiment of FIG. 7.

The second anchoring unit 850b, the fourth anchoring unit 850d, and the fifth anchoring unit 850e are arranged in a combination arrangement 855. The combination arrangement 855 includes a distal end portion 898, a proximal end portion 897, a wide middle portion 899a, and a narrow middle portion 899b. The distal end portion 898 of the combination arrangement 855 is defined by the narrow end portion of the fourth anchoring unit 850d. The distal end portion 898 has a largest outer radius at the end thereof. The proximal end portion 897 of the combination arrangement 855 is defined by the wide end portion of the fifth anchoring unit 850e. The proximal end portion 897, of the illustrated embodiment, has an outer radius of the distal end portion that varies and defines a largest outer radius. Further, the wide middle portion 899a is defined by a combination of wide end portions of the second anchoring unit 850a and the fourth anchoring unit 850d disposed adjacent to each other. The narrow middle portion 899b is defined by a combination of narrow end portions of the second anchoring unit 850b and the fifth anchoring unit 850e. The narrow middle portion 899b is between the proximal end portion 897 and the wide middle portion 899a, and the wide middle portion is between the distal end portion 898 and the narrow middle portion 899a. Similarly, the wide middle portion 899a and the narrow middle portion 899b each have a largest outer radius.

In the illustrated embodiment, the largest outer radius of each of the proximal end portion 897 and the wide middle portion 899a of the combination arrangement 855 is larger than the largest outer radius of each of the distal end portion 898 and the narrow middle portion 899b of the combination arrangement 855.

In some embodiments, the first and third anchoring units 850a, 850c may be formed as a unitary structure. Similarly, the second, fourth, and fifth anchoring units 850b, 850d, 850e (or any combination thereof) may be formed as a unitary structure. In other embodiments, the anchoring units 850a, 850b, 850c, 850d, and 850e can be formed separately as discrete elements.

Figure 9:
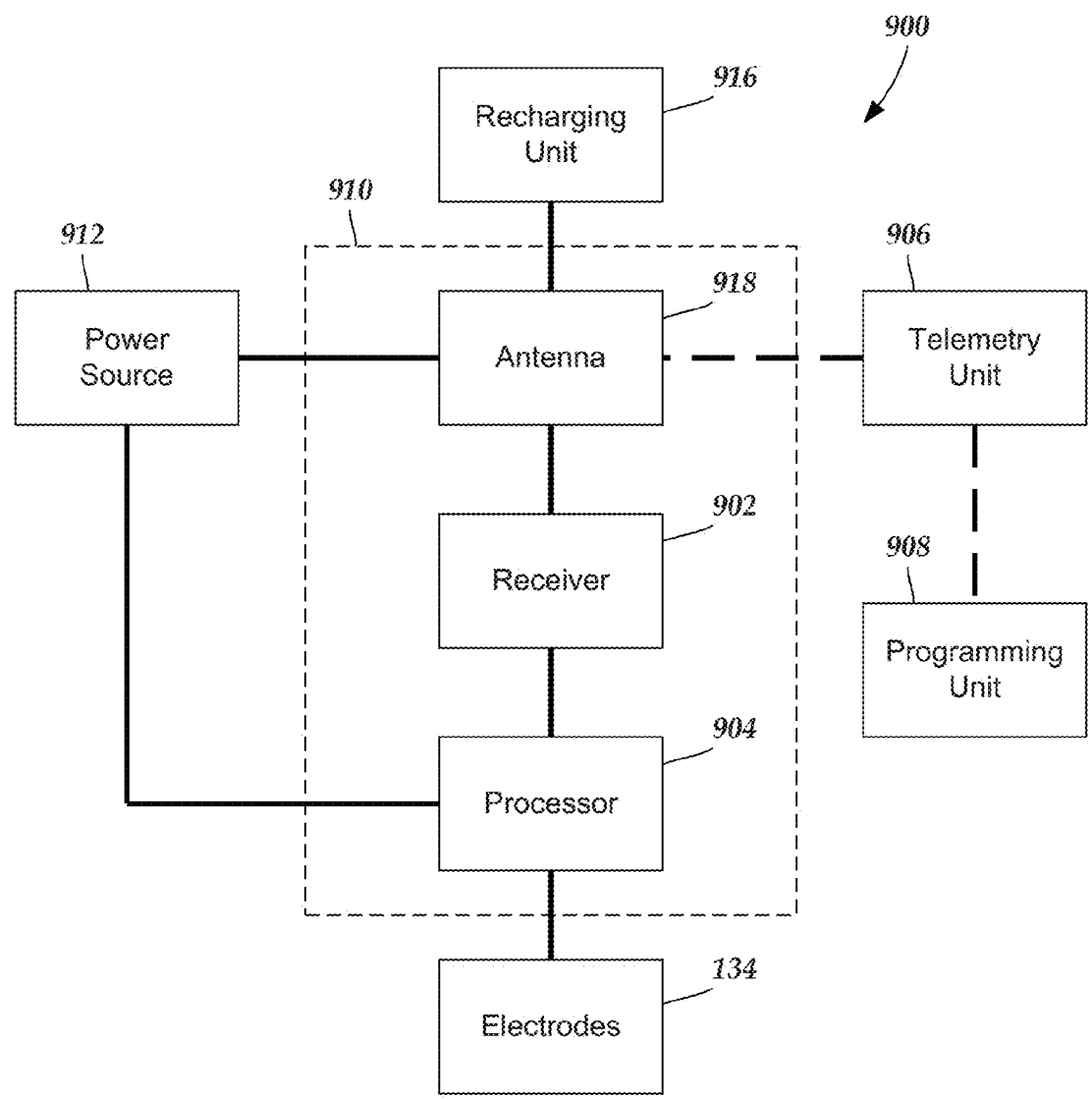
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, a power source 912, an antenna 918, a receiver 902, and a processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 9,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 selects which electrode(s) are cathodes and which electrode(s) are anodes. In some embodiments, the processor 904 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by the programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and the receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include the antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   a lead body having a distal end portion, a proximal end portion, and a longitudinal length;
   a plurality of electrodes disposed along the distal end portion of the lead body;
   a plurality of terminals disposed along the proximal end portion of the lead body;
   a plurality of conductors electrically coupling the terminals to the electrodes; and
   a plurality of anchoring units disposed along the distal end portion of the lead body, the plurality of anchoring units comprising a first anchoring unit and a second anchoring unit, wherein the first and second anchoring units each comprise a wide end portion and a narrow end portion, wherein a largest outer radius of the wide end portion is larger than a largest outer radius of the narrow end portion,
   wherein the first anchoring unit is disposed closer to the proximal end portion of the lead body than any other of the plurality of anchoring units, wherein the wide end portion of the first anchoring unit is disposed closer to the proximal end portion of the lead body than the narrow end portion of the first anchoring unit and the narrow end portion of the second anchoring unit is disposed closer to the proximal end portion of the lead body than the wide end portion of the second anchoring unit, and wherein at least one of the electrodes is disposed distal to all of the anchoring units.

2. The electrical stimulation lead of claim 1, wherein the plurality of anchoring units further comprises a third anchoring unit disposed adjacent the first anchoring unit, wherein the third anchoring unit comprises a wide end portion and a narrow end portion, wherein a largest outer radius of the wide end portion is larger than a largest outer radius of the narrow end portion, wherein the narrow end portion of the third anchoring unit is disposed closer to the proximal end portion of the lead body than the wide end portion of the third anchoring unit.

3. The electrical stimulation lead of claim 1, wherein the plurality of anchoring units further comprises a fourth anchoring unit disposed adjacent, and distal to, the second anchoring unit, wherein the fourth anchoring unit comprises a wide end portion and a narrow end portion, wherein a largest outer radius of the wide end portion is larger than a largest outer radius of the narrow end portion, wherein the wide end portion of the fourth anchoring unit is disposed closer to the proximal end portion of the lead body than the narrow end portion of the fourth anchoring unit.

4. The electrical stimulation lead of claim 3, wherein the plurality of anchoring units further comprises a fifth anchoring unit disposed adjacent, and proximal to, the second anchoring unit, wherein the fifth anchoring unit comprises a wide end portion and a narrow end portion, wherein a largest outer radius of the wide end portion is larger than a largest outer radius of the narrow end portion, wherein the wide end portion of the fifth anchoring unit is disposed closer to the proximal end portion of the lead body than the narrow end portion of the fifth anchoring unit.

5. An electrical stimulation lead, comprising:
   a lead body having a distal end portion, a proximal end portion, and a longitudinal length;
   a plurality of electrodes disposed along the distal end portion of the lead body;
   a plurality of terminals disposed along the proximal end portion of the lead body;
   a plurality of conductors electrically coupling the terminals to the electrodes; and
   a plurality of anchoring units disposed along the distal end portion of the lead body, the plurality of anchoring units comprising a first anchoring unit and a second anchoring unit, wherein the first and second anchoring units each comprise a wide end portion and a narrow end portion, wherein a largest outer radius of the wide end portion is larger than a largest outer radius of the narrow end portion, wherein the first anchoring unit is disposed closer to the proximal end portion of the lead body than any other of the plurality of anchoring units, wherein the wide end portion of the first anchoring unit is disposed closer to the proximal end portion of the lead body than the narrow end portion of the first anchoring unit and the narrow end portion of the second anchoring unit is disposed closer to the proximal end portion of the lead body than the wide end portion of the second anchoring unit, and wherein at least one of the electrodes is disposed proximal to all of the anchoring units.

6. The electrical stimulation lead of claim 1, wherein at least one of the electrodes is disposed between the first anchoring unit and the second anchoring unit.

7. The electrical stimulation lead of claim 1, where each of the plurality of anchoring units comprises a lead attachment element and a plurality of fins, each fin attached to, and extending away from, the lead attachment element.

8. An electrical stimulating system comprising:
the electrical stimulation lead of claim 1;
a control module coupleable to the electrical stimulation lead, the control module comprising
a housing, and
an electronic subassembly disposed in the housing; and
a connector for receiving the electrical stimulation lead, the connector having a proximal end a distal end, and a longitudinal length, the connector comprising
a connector housing defining a port at the distal end of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals disposed along the proximal end portion of the lead body of the electrical stimulation lead.

9. The electrical stimulation lead of claim 1, wherein
at least one of the anchoring units forms a wide end arrangement, the wide end arrangement comprising a distal end portion, a proximal end portion, and a middle portion,
wherein the proximal end portion and distal end portion of the wide end arrangement each have a largest outer radius that is larger than a largest outer radius of the middle portion of the wide end arrangement.

10. The electrical stimulation lead of claim 9, wherein at least one of the anchoring units forms a wide center arrangement, the wide center arrangement comprising a distal end portion, a proximal end portion, and a middle portion, wherein the proximal end portion and distal end portion of the wide center arrangement each have a largest outer radius that is smaller than a largest outer radius of the middle portion of the wide center arrangement.

11. The electrical stimulation lead of claim 9, wherein at least one of the anchoring units forms a combination arrangement, the combination arrangement comprising a distal end portion, a proximal end portion, a wide middle portion, and a narrow middle portion, wherein the proximal end portion and the wide middle portion of the combination arrangement each have a largest outer radius that is larger than a largest outer radius of each of the distal end portion and the narrow middle portion of the combination arrangement, wherein the narrow middle portion is positioned between the proximal end portion and the wide middle portion and the wide middle portion is positioned between the distal end portion and the narrow middle portion.

12. The electrical stimulation lead of claim 9, wherein the wide end arrangement is formed by two of the anchoring units.

13. The electrical stimulation lead of claim 9, where each of the plurality of anchoring units comprises a lead attachment element and a plurality of fins, each fin attached to, and extending away from, the lead attachment element.

14. An electrical stimulation lead, comprising:
a lead body having a distal end portion, a proximal end portion, and a longitudinal length;
a plurality of electrodes disposed along the distal end portion of the lead body;
a plurality of terminals disposed along the proximal end portion of the lead body;
a plurality of conductors electrically coupling the terminals to the electrodes; and
a plurality of anchoring units disposed along the distal end portion of the lead body, each of the anchoring units comprising a lead attachment element and a plurality of fins, each fin attached to, and extending away from, the lead attachment element, the plurality of anchoring units comprising a first anchoring unit and a second anchoring unit, wherein the first and second anchoring units each comprise a wide portion where the fins extend furthest from the lead attachment element and a narrow portion where the fins extend least from the lead attachment element,
wherein the first anchoring unit is disposed closer to the proximal end portion of the lead body than any other of the plurality of anchoring units, wherein the wide portion of the first anchoring unit is disposed closer to the proximal end portion of the lead body than the narrow portion of the first anchoring unit and the narrow portion of the second anchoring unit is disposed closer to the proximal end portion of the lead body than the wide portion of the second anchoring unit, and wherein at least one of the electrodes is disposed distal to all of the anchoring units.

15. The electrical stimulation lead of claim 14, wherein the plurality of anchoring units further comprises a third anchoring unit disposed adjacent the first anchoring unit, wherein the third anchoring unit comprises a wide portion where the fins extend furthest from the lead attachment element and a narrow portion where the fins extend least from the lead attachment element, wherein the narrow portion of the third anchoring unit is disposed closer to the proximal end portion of the lead body than the wide portion of the third anchoring unit.

16. The electrical stimulation lead of claim 15, wherein the first and third anchoring units form a wide end arrangement comprising a distal end portion, a proximal end portion, and a middle portion, wherein the proximal end portion and distal end portion of the wide end arrangement each have a largest outer radius that is larger than a largest outer radius of the middle portion of the wide end arrangement.

17. The electrical stimulation lead of claim 14, wherein the plurality of anchoring units further comprises a fourth anchoring unit disposed adjacent, and distal to, the second anchoring unit, wherein the fourth anchoring unit comprises a wide portion where the fins extend furthest from the lead attachment element and a narrow portion where the fins extend least from the lead attachment element, wherein the wide portion of the fourth anchoring unit is disposed closer to the proximal end portion of the lead body than the narrow end portion of the fourth anchoring unit.

18. The electrical stimulation lead of claim 17, wherein the second and fourth anchoring units form a wide center arrangement comprising a distal end portion, a proximal end portion, and a middle portion, wherein the proximal end portion and distal end portion of the wide end arrangement each have a largest outer radius that is smaller than a largest outer radius of the middle portion of the wide end arrangement.

19. The electrical stimulation lead of claim 17, wherein the plurality of anchoring units further comprises a fifth anchoring unit disposed adjacent, and proximal to, the second anchoring unit, wherein the fifth anchoring unit comprises a wide portion where the fins extend furthest from the lead attachment element and a narrow portion where the fins extend least from the lead attachment element, wherein the wide portion of the fifth anchoring unit is disposed closer to the proximal end portion of the lead body than the narrow end portion of the fifth anchoring unit.

20. The electrical stimulation lead of claim 19, wherein the second, fourth, and fifth anchoring units form a combination arrangement comprising a distal end portion, a proximal end portion, a wide middle portion, and a narrow middle portion, wherein the proximal end portion and the wide middle portion of the combination arrangement each have a largest outer radius that is larger than a largest outer radius of each of the distal end portion and the narrow middle portion of the combination arrangement, wherein the narrow middle portion is between the proximal end portion and the wide middle portion and the wide middle portion is between the distal end portion and the narrow middle portion.

\* \* \* \* \*